(12) United States Patent
Duvert et al.

(10) Patent No.: US 12,083,253 B2
(45) Date of Patent: Sep. 10, 2024

(54) AROMA GENERATOR

(71) Applicant: SONY GROUP CORPORATION, Tokyo (JP)

(72) Inventors: Cedric Duvert, Tokyo (JP); Hideaki Tachino, Tokyo (JP); Yukito Inoue, Tokyo (JP); Shuji Fujita, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 566 days.

(21) Appl. No.: 17/291,031

(22) PCT Filed: Aug. 7, 2019

(86) PCT No.: PCT/JP2019/031179
§ 371 (c)(1),
(2) Date: May 4, 2021

(87) PCT Pub. No.: WO2020/100362
PCT Pub. Date: May 22, 2020

(65) Prior Publication Data
US 2021/0369904 A1    Dec. 2, 2021

(30) Foreign Application Priority Data
Nov. 14, 2018   (JP) ................................ 2018-214058

(51) Int. Cl.
*A61L 9/12*      (2006.01)
*A42B 3/28*      (2006.01)
*B60H 3/00*      (2006.01)

(52) U.S. Cl.
CPC .............. *A61L 9/125* (2013.01); *A42B 3/286* (2013.01); *B60H 3/0035* (2013.01);
(Continued)

(58) Field of Classification Search
CPC .............. A61L 9/125; A61L 2209/111; A61L 2209/133; A61L 2209/135; A42B 3/286; B60H 3/0035; B60H 2003/0064
See application file for complete search history.

(56) References Cited

U.S. PATENT DOCUMENTS 6,167,574 B1   1/2001  Hayashida
8,448,739 B2   5/2013  Kolich
(Continued)

FOREIGN PATENT DOCUMENTS

AU    2016279192 A1    1/2018
CN    102039897 A      5/2011
(Continued)

OTHER PUBLICATIONS

Machine Translation of JP 11278048 (Year: 1999).*
(Continued)

*Primary Examiner* — Lessanework Seifu
(74) *Attorney, Agent, or Firm* — CHIP LAW GROUP (57) ABSTRACT

An aroma generator including a cartridge holding unit equipped with a cartridge that holds a fragrance, and a control unit that automatically selects a type of the fragrance in the cartridge according to sensing information obtained from the outside. The sensing information may be external environment information and/or biological information. Furthermore, the aroma generator may further include an air blower that blows the fragrance in the cartridge, and the control unit may automatically change blowing intensity of the air blower according to the sensing information.

16 Claims, 6 Drawing Sheets

(52) U.S. Cl.
CPC .... *A61L 2209/111* (2013.01); *A61L 2209/133* (2013.01); *A61L 2209/135* (2013.01); *B60H 2003/0064* (2013.01)

(56) References Cited

U.S. PATENT DOCUMENTS

| | | |
|---|---|---|
| 2011/0089255 A1 | 4/2011 | Kolich |
| 2017/0098121 A1 | 4/2017 | Ur |
| 2018/0169288 A1 | 6/2018 | Kelsen |
| 2018/0318461 A1 | 11/2018 | Nishimaki et al. |
| 2019/0160195 A1 | 5/2019 | Kelsen |
| 2021/0027050 A1 | 1/2021 | Ur |

FOREIGN PATENT DOCUMENTS

| | | |
|---|---|---|
| CN | 106255515 A | 12/2016 |
| CN | 107921167 A | 4/2018 |
| CN | 108079360 A | 5/2018 |
| EP | 3316917 A1 | 5/2018 |
| IL | 231686 A | 4/2016 |
| JP | 10-008321 A | 1/1998 |
| JP | 11-278048 A | 10/1999 |
| JP | 2000-192319 A | 7/2000 |
| JP | 2014-67293 A | 4/2014 |
| JP | 2016-097736 A | 5/2016 |
| JP | 6990812 B2 | 1/2022 |
| KR | 10-2018-0041658 A | 4/2018 |
| WO | 2015/145452 A1 | 10/2015 |
| WO | 2016/205836 A1 | 12/2016 |
| WO | WO-2017086571 A1 | 5/2017 |
| WO | 2017/098748 A1 | 6/2017 |
| WO | 2018/022562 A1 | 2/2018 |
| WO | 2018/070456 A1 | 4/2018 |

OTHER PUBLICATIONS

International Search Report and Written Opinion of PCT Application No. PCT/JP2019/031179, issued on Sep. 17, 2019, 10 pages of ISRWO.

Extended European Search Report of EP Application No. 19885897.9, issued on Mar. 31, 2022, 09 pages.

* cited by examiner

AROMA GENERATOR

CROSS REFERENCE TO RELATED APPLICATIONS

This application is a U.S. National Phase of International Patent Application No. PCT/JP2019/031179 filed on Aug. 07, 2019, which claims priority benefit of Japanese Patent Application No. JP 2018-214058 filed in the Japan Patent Office on Nov. 14, 2018. Each of the above-referenced applications is hereby incorporated herein by reference in its entirety.

TECHNICAL FIELD

The present technology relates to an aroma generator.

BACKGROUND ART

Conventionally, techniques related to a device capable of generating an aroma have been proposed. For example, Patent Document 1 proposes a technique of providing an aroma by supplying air to a storage device storing a fragrance holder and releasing the vaporized fragrance by a flow of the air.

CITATION LIST

Patent Document

Patent Document 1: Japanese Patent Application Laid-Open No. 2014-67293

SUMMARY OF THE INVENTION

Problems to be Solved by the Invention

However, there have been the circumstances according to the conventional techniques that, for example, an aroma cannot be automatically provided to a user from a device for the purpose of a reminder of drowsy driving and the like, and further development of the aroma generator has been desired.

In view of the above, it is a main object of the present technology to provide a novel aroma generator.

Solutions to Problems

That is, first, the present technology provides an aroma generator including: a cartridge holding unit equipped with a cartridge that holds a fragrance; and a control unit that automatically selects a type of the fragrance in the cartridge according to sensing information obtained from the outside.

In the present technology, the sensing information may be external environment information and/or biological information.

Furthermore, in the present technology, there may be further included an air blower that blows the fragrance in the cartridge, and the control unit may automatically change blowing intensity of the air blower according to the sensing information. In this case, the aroma generator according to the present technology may include a plurality of the air blowers. Furthermore, in this case, the control unit may control blowing timing and/or a blowing time from the air blower.

Moreover, the aroma generator according to the present technology may further include a display unit that displays information associated with the cartridge and/or the sensing information. In this case, the control unit may wirelessly communicate with the display unit.

In addition, in the present technology, there may be further included an operation unit that selects a type of the fragrance in the cartridge. In this case, the operation unit may select a type of the fragrance in the cartridge using an application.

Furthermore, the aroma generator according to the present technology may be attached to a mobile object. In this case, the mobile object may be a car, a motorcycle, or a bicycle. Furthermore, in this case, the sensing information may be any one or more pieces of information selected from a group including a speed, an acceleration level, and an angle with the ground of the car, the motorcycle, or the bicycle.

Moreover, the aroma generator according to the present technology may be attached to clothing or a helmet.

In addition, the control unit may wirelessly communicate with an external network to cause AI on the external network to perform machine learning.

Furthermore, the present technology also provides an aroma generator including: a cartridge holding unit equipped with a cartridge that holds a fragrance; a sensing unit that obtains sensing information; and a control unit that automatically selects a type of the fragrance in the cartridge according to the sensing information obtained by the sensing unit.

MODE FOR CARRYING OUT THE INVENTION

Hereinafter, preferred embodiments for implementing the present technology will be described with reference to the accompanying drawings.

The embodiments to be described below show examples of typical embodiments of the present technology, and the scope of the present technology is not narrowly interpreted by them. Note that descriptions will be given in the following order.

1. Aroma Generator 1000
 (1) Cartridge Holding Unit 1
 (1-1) Cartridge 11
 (2) Control Unit 2
 (2-1) First Specific Example
 (2-2) Second Specific Example
 (2-3) Third Specific Example
 (2-4) Other Specific Examples
 (3) Air Blower 3
 (3-1) Specific Example 4
 (4) Display Unit 4
 (5) Operation Unit 5
2. Variation of Aroma Generator 1000
 (1) Sensing Unit 6

1. Aroma Generator 1000

Figure 1:
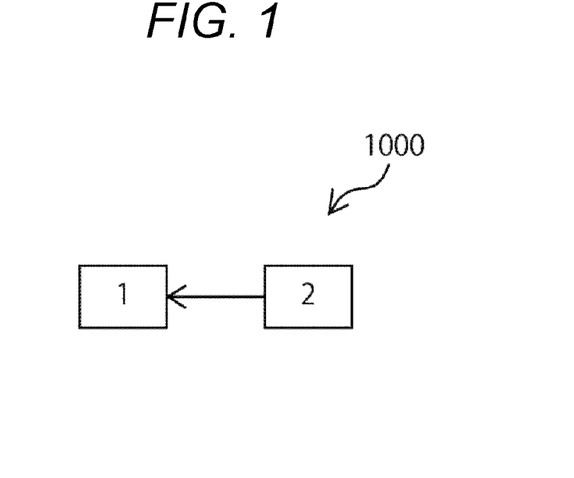
FIG. 1 is a conceptual diagram illustrating an exemplary configuration of an aroma generator 1000.

FIG. 1 is a conceptual diagram illustrating an exemplary configuration of an aroma generator 1000. The aroma generator 1000 according to the present technology includes a cartridge holding unit 1 and a control unit 2. Furthermore, an air blower 3, a display unit 4, an operation unit 5, and the like may be provided, as necessary. Hereinafter, each part will be detailed.

(1) Cartridge Holding Unit 1

Figure 2:
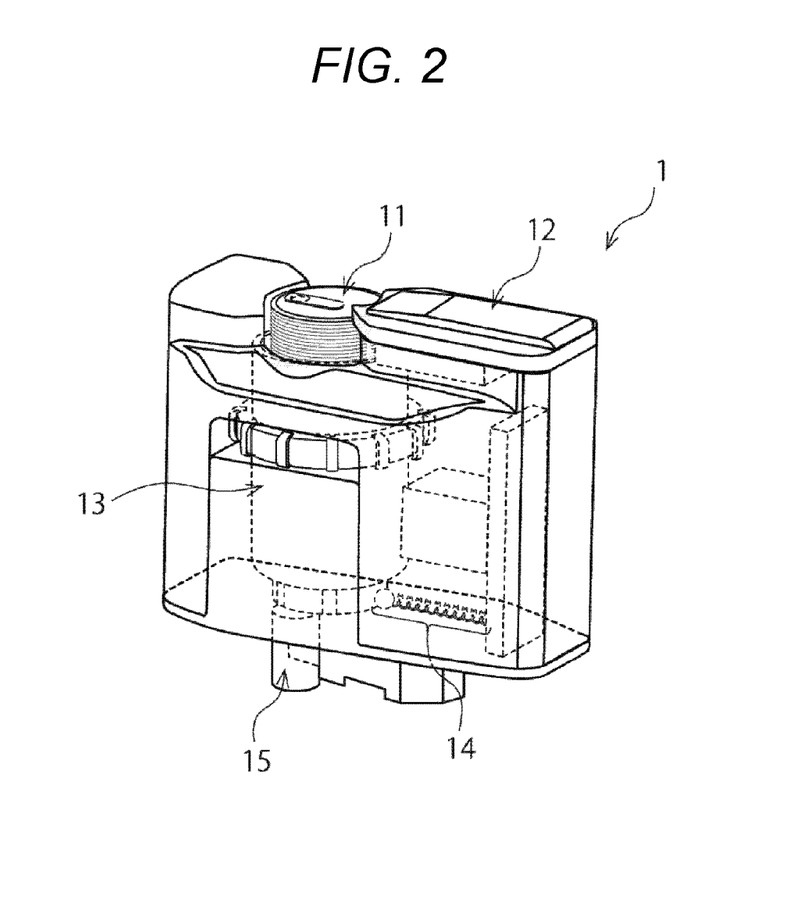
FIG. 2 is a perspective view illustrating an exemplary embodiment of a cartridge holding unit 1.
Figure 3:
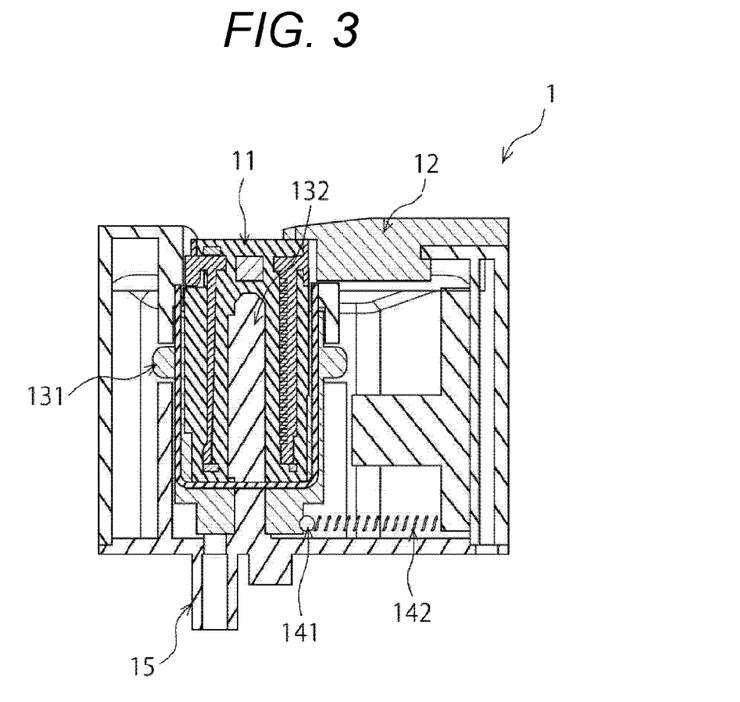
FIG. 3 is a cross-sectional view of the cartridge holding unit 1 according to the embodiment illustrated in FIG. 2.

The cartridge holding unit 1 includes a cartridge 11 holding a fragrance. FIG. 2 is a perspective view illustrating an exemplary embodiment of the cartridge holding unit 1, and FIG. 3 is a cross-sectional view of the cartridge holding unit 1 according to the embodiment illustrated in FIG. 2. In the embodiment illustrated in FIGS. 2 and 3, the cartridge holding unit 1 includes, in addition to the cartridge 11, a cartridge fixing mechanism 12, a cartridge holder 13, a cartridge holder fixing mechanism 14, and an air-blowing flow path 15.

The shape of the cartridge 11 is not particularly limited, and may be, for example, a cylindrical shape. The cartridge 11 is provided with a plurality of ventilation flow paths 110 through which air supplied from a ventilation source passes. A fragrance is held in a wet condition in the ventilation flow path 110. The fragrance is held in a state of being attached to the inner surface of the ventilation flow path 110. The fragrance may be, for example, an essential oil, an essential oil diluted with ethanol, or the like. One or a plurality of ventilation flow paths 110 may be provided. Although the cartridge 11 having five ventilation flow paths 110 is used in the present embodiment, the present technology is not limited thereto. The cartridge 11 will be detailed later.

The shape of the cartridge fixing mechanism 12 is not particularly limited as long as the structure is such that the cartridge 11 does not protrude from the cartridge holder 13. For example, as illustrated in FIG. 2, it may be a structure in which the cartridge 11 is pressed and fixed.

The cartridge holder 13 is a part into which the cartridge 11 is inserted, and includes a rotary dial 131 and a rotary shaft 132 as illustrated in FIG. 3. The aroma can be switched by rotating the cartridge 11 around the rotary shaft 132 with signals from the control unit 2 to be described later. Note that the rotary shaft 132 can also be used as a positioning mechanism for the cartridge 11.

Grooves of the number same as the number of the ventilation flow paths 110 of the cartridge 11 are provided at regular intervals on the bottom surface of the cartridge holder 13. One of the ventilation flow paths 110 communicates with the air-blowing flow path 15 to be described later in a state where the rotary dial 131 is locked in the locking groove. Therefore, it is possible to switch the ventilation flow path 110 that communicates with the air-blowing flow path 15 by rotating the rotary dial 131.

Furthermore, the cartridge holder 13 may be provided with a locking protrusion that engages with a locking groove 114 of the cartridge 11 on the inner peripheral surface thereof.

The cartridge holder fixing mechanism 14 may include, for example, a fixing ball 141 and a spring 142, and is configured in such a manner that the spring 142 shrinks while the cartridge 11 is rotated, and is fixed when the desired angle is reached.

The air-blowing flow path 15 is a part through which the sent air flows, and air is sent to the cartridge 11 in the cartridge holder 13 through the air-blowing flow path 15. The air-blowing flow path 15 may be connected to the air blower 3 to be described later by an air-blowing pipe 30.

Note that, although illustration is omitted, the cartridge holding unit 1 may be provided with a reader capable of reading the contents of the cartridge 11. In this case, the cartridge 11 may be provided with a label, a bar code, or the like.

(1-1) Cartridge 11

Figure 4:
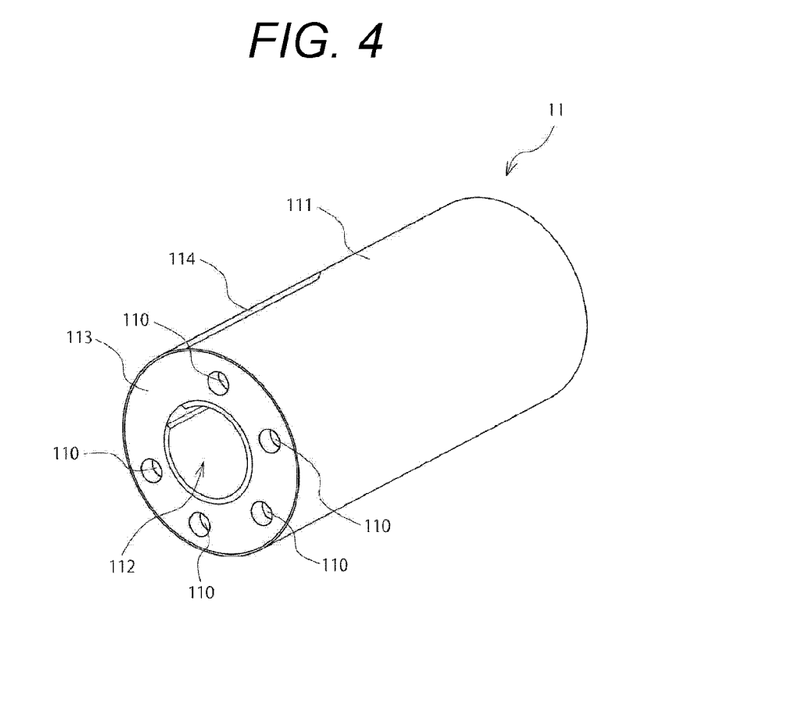
FIG. 4 is a perspective view illustrating an exemplary embodiment of a cartridge 11.

Hereinafter, the cartridge 11 that can be used in the aroma generator 1000 according to the present embodiment will be described with reference to FIG. 4.

The cartridge 11 includes a main body 111, an axial hole 112, and a plurality of ventilation flow paths 110. The main body 111 has a cylindrical outer shape. The main body 111 is provided with the axial hole 112 centered on the axial center. The axial hole 112 can be used as a guide at the time of being mounted in the cartridge holder 13. Note that the outer shape of the fragrance cartridge 11 is not limited to the cylindrical shape illustrated in FIG. 4, and may be, for example, a shape of a circular cylinder, a rectangular parallelepiped, a cube, or any other appropriate shape.

For example, an essential oil or a liquid fragrance obtained by diluting the essential oil with ethanol is attached and held in a wet condition on at least a part of the inner surface of each ventilation flow path 110. For example, a liquid fragrance is filled in the ventilation flow path 110, and then a high-pressure gas such as air is supplied into the ventilation flow path 110 for a predetermined time, whereby excess liquid fragrance is ejected and the fragrance can be attached in a wet condition onto the inner surface of the ventilation flow path 110. In the cartridge 11 according to the present embodiment, the liquid fragrance is not filled in the ventilation flow path 110, and it is unlikely that the liquid fragrance leaks from the cartridge 11.

The ventilation flow paths 110 are arranged at regular intervals around the axial center of the main body 111. With this arrangement, it is possible to switch the ventilation flow path 110 through which air flows by rotating the cartridge 11 around the axis at a constant rotation angle. Fragrances to be held in the respective ventilation flow paths 110 may be all the same, or may be partially or wholly different. In a case where different fragrances are held in the respective ventilation flow paths 110, an aroma to be released can be switched by switching the ventilation flow path 110 capable of supplying air.

In the cartridge 11 according to the present embodiment, while five ventilation flow paths 110 are arranged at regular intervals of 60 degrees, one ventilation flow path is labor-saving. A part 113 where formation of the ventilation flow path is omitted is positioned at the aroma outlet while the aroma generator 1 is not used so that the aroma does not escape from the cartridge 11. Note that the number of the ventilation flow paths 110 is not limited to five as illustrated in FIG. 4.

The main body 111 of the cartridge 11 may include an organic polymeric material so that the fragrance including an essential oil or the like easily infiltrates, for example. Examples of the organic polymeric material may include any one of polyvinyl chloride, polyethylene, phenolic resin, olefin resin, nylon, polyester, synthetic rubber, silicon resin, natural rubber, protein, nucleic acid, lipid, and polysaccharide, or a mixture thereof. However, the main body 111 is not limited to those examples. For example, one or more materials selected from polymeric resins such as acryl resin, urethane resin, acrylonitrile-butadiene-styrene (ABS) resin, polyether ether ketone (PEEK) resin, polyacetal (POM) resin, fluorine resin, cycloolefin polymer resin, and polyimide resin, metals such as stainless steel and aluminum, inorganic crystals such as quartz, or glass may be used.

Note that the cartridge 11 can also be manufactured using, for example, a 3D printer, and in this case, a material suitable for the 3D printer may be selected as a constituent material of the cartridge 11.

The cartridge 11 has the locking groove 114 on the outer peripheral surface of the main body 111. The locking groove 114 is used for positioning the cartridge holder 13 and the cartridge 11 together with the locking protrusion provided on the inner peripheral surface of the cartridge holder 13. Furthermore, with the locking groove 114 and the locking protrusion fitting with each other, the relative rotation between the cartridge holder 13 and the cartridge 11 becomes impossible, whereby the cartridge holder 13 and the cartridge 11 can rotate as a unit.

(2) Control Unit 2

The control unit 2 automatically selects a type of the fragrances in the cartridge 11 according to sensing information obtained from the outside.

In the present specification, the "sensing information" indicates information obtained by using a sensor (detector). While examples of the sensor include a speed sensor, an acceleration sensor, a gyroscope sensor, a global positioning system (GPS), a direction sensor, a magnetic field sensor, a gravity sensor, an illuminance sensor, a distance sensor, a temperature sensor, a volume sensor, a motion sensor, a rain sensor, an odor sensor, a gas sensor, and a biological sensor (e.g., body temperature sensor, blood pressure sensor, heart rate sensor, sweating amount sensor, vibration sensor, brain wave sensor, body motion detection sensor, blood concentration sensor, electro-oculography sensor, pupil sensor, etc.), they are not limited thereto in the present technology. Note that those sensors may be used alone or in combination of two or more in the present technology.

Examples of the sensing information include external environment information and/or biological information. Examples of the external environment information include a temperature, humidity, a speed, an acceleration level, an angular speed, an angle with the ground, a direction, a magnetic field, a latitude/longitude, an altitude, luminous intensity, illuminance, a volume, a frequency, a wind pressure, lateral G, and an inter-vehicular distance. Examples of the biological information include a blood pressure, brain waves, a body temperature, a sweating amount, pupil opening, a blood oxygen concentration, a body motion, a respiratory count, and a respiratory rate. Note that those pieces of information may be used alone or in combination of two or more in the present technology.

While signal transmission from the sensor can be wired communication or wireless communication in the present technology, wireless communication is preferable because disconnection is unlikely to occur and the device configuration can be simplified. Examples of the wireless communication include communication using infrared rays, communication using radio waves such as Bluetooth (registered trademark) and Wi-Fi (registered trademark), communication using electromagnetic waves such as visible light communication.

Furthermore, in the present technology, the control unit 2 can wirelessly communicate with an external network and cause the AI on the external network to perform machine learning. With this arrangement, a user's favorite aroma can be learned, and the user's favorite aroma can be provided. Note that the AI may be uploaded on a cloud.

Figure 5:
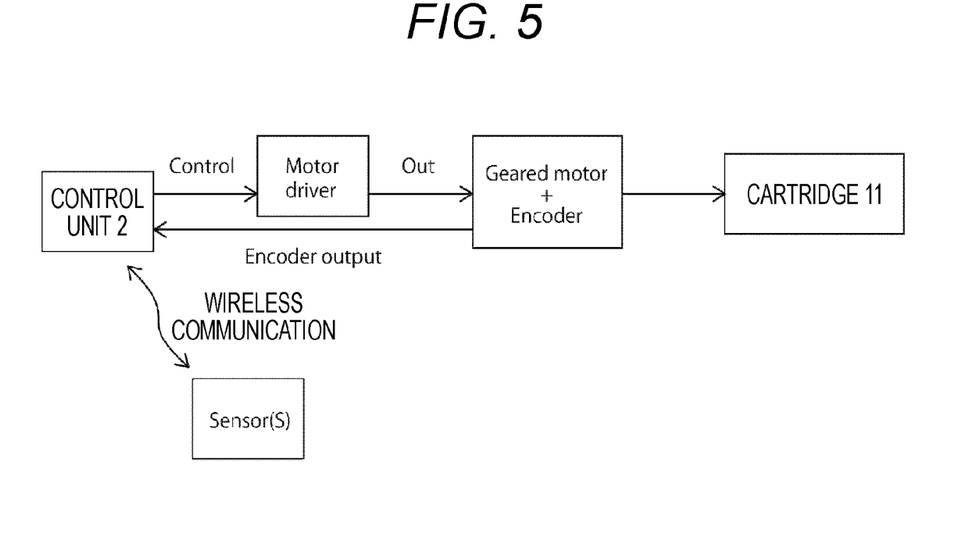
FIG. 5 is a conceptual diagram illustrating exemplary control by a control unit 2.

Exemplary control by the control unit 2 will be described with reference to FIG. 5. First, the control unit 2 receives sensing information from one or a plurality of sensors by wireless communication. Thereafter, the control unit 2 selects a predetermined fragrance from the received sensing information, and provides a motor driver side with a command for controlling electric power to be applied to a geared motor. Then, the motor driver applies predetermined electric power to the geared motor to drive the geared motor. The geared motor rotates the cartridge 11 to select a predetermined fragrance stored in the cartridge 11. An encoder is attached to the geared motor, and the encoder is capable of outputting, to the control unit 2, a rotation amount, a rotation speed, a rotation position, a rotation angle, and the like of the geared motor to adjust them.

(2-1) First Specific Example

Hereinafter, control by the control unit 2 will be described more specifically.

First, the control unit 2 obtains, by wireless communication, information associated with the number of blinks, which is one of biological information, from a predetermined sensor. This information includes, for example, that equal to or more than 25 blinks have been confirmed within one minute or the like. In response to this information, as the number has exceeded a predetermined reference value (=the number of blinks is equal to or more than 20 within one minute), the control unit 2 determines that the user is feeling drowsiness and it is required to reduce the drowsiness of the user, and selects an aroma of peppermint from the fragrances held in the cartridge 11. Then, the control unit 2 rotates the cartridge 11 in the cartridge holding unit 1 using the geared motor and the encoder so that the aroma is released toward the user.

(2-2) Second Specific Example

An example different from the first specific example described above will be described.

The present second specific example is an exemplary case where the aroma generator 1000 is attached to a mobile object. The mobile object to which the aroma generator 1000 is attached is not particularly limited, and may be, for example, a car, a motorcycle, or a bicycle.

First, the control unit 2 obtains, by wireless communication, information associated with the number of repetitions of stopping based on the accelerator and the brake, which is one of external environment information, from a predetermined sensor. This information includes, for example, that equal to or more than four repetitions of stopping based on the accelerator and the brake have been confirmed within one minute or the like. In response to this information, as the number has exceeded a predetermined reference value (=the number of repetitions of stopping based on the accelerator and the brake is equal to or more than four), the control unit 2 determines that the user is in traffic congestion and it is required to relieve irritation caused by the congestion, and selects an aroma with a relaxing effect from the fragrances held in the cartridge 11. Then, the control unit 2 rotates the cartridge 11 in the cartridge holding unit 1 using the geared motor and the encoder so that the aroma is released toward the user.

With the aroma generator 1000 attached to the mobile object in this manner, it becomes possible to eliminate, prevent, or improve the states such as fatigue, dozing, desolation, distraction, and apnea while driving. As a result, the changes brought about by the aroma can keep a driver agile and astute. Furthermore, the aroma generator 1000 according to the present technology is hands-free, whereby the aroma can be enjoyed without disturbing driving operation of the mobile object.

Furthermore, in a case where the aroma generator 1000 is attached to a car in the present technology, the aroma generator 1000 may be attached to each seat to provide a different aroma for each seat according to the sensing information of each seat. In this case, for example, it is possible to provide a driver with an aroma having an effect of enhancing concentration, and to provide an occupant with an aroma having a relaxing effect.

(2-3) Third Specific Example

An example different from the first and second specific examples described above will be described.

The present third specific example is an exemplary case where the aroma generator 1000 is attached to a mobile object in a similar manner to the second specific example described above. In this case, in the present technology, the sensing information may be any one or more pieces of information selected from a group including a speed, an acceleration level, and an angle with the ground of the mobile object. The present third specific example is an exemplary case where the sensing information is set to, among those pieces of information, an angle with the ground.

First, the control unit 2 obtains, by wireless communication, information associated with the angle with the ground, which is one of external environment information, from a predetermined sensor. This information includes, for example, that the average angle with the ground (average cornering angle) within 30 seconds has been 105 degrees or the like. In response to this information, as the angle has exceeded a predetermined reference value (=the average angle within 30 seconds is equal to or more than 90 degrees), the control unit 2 determines that the user is passing a slope and it is required to increase the user's concentration, and selects an aroma with an effect of increasing concentration from the fragrances held in the cartridge 11. Then, the control unit 2 rotates the cartridge 11 in the cartridge holding unit 1 using the geared motor and the encoder so that the aroma is released toward the user.

Note that, in the present technology, in a case where the control unit 2 receives a plurality of pieces of sensing information simultaneously, the control unit 2 may be set to prioritize those pieces of information. In the case of the example described above, in a case where the control unit 2 has received three pieces of sensing information including that equal to or more than 25 blinks have been confirmed within one minute, that equal to or more than four repetitions of stopping based on the accelerator and the brake have been confirmed within one minute, and that the average cornering angle within 30 seconds has been 105 degrees, the information indicating that equal to or more than 25 blinks have been confirmed within one minute may be preferentially applied putting emphasis on safety standards, and measures against drowsiness of the user may be prioritized.

Furthermore, in the present technology, the aroma generator 1000 may have an alert function by ejecting a predetermined aroma to the user on the basis of external environment information such as traffic congestion and an accident.

(2-4) Other Specific Examples

Hereinafter, other specific examples will be described.

The aroma generator 1000 according to the present technology may be attached not only to a mobile object but also to clothing or a helmet. In the present technology, examples of the clothing include, but are not limited to, jackets, dress shirts, coats, T-shirts, sweat shirts, sweaters, sweat suits, one-piece suits, dresses, hats, kerchiefs, bandanas, scarves, and ties. Furthermore, the aroma generator 1000 according to the present technology can be attached to and detached from the clothing or the helmet, and can be appropriately replaced and used, as necessary.

Figure 6:
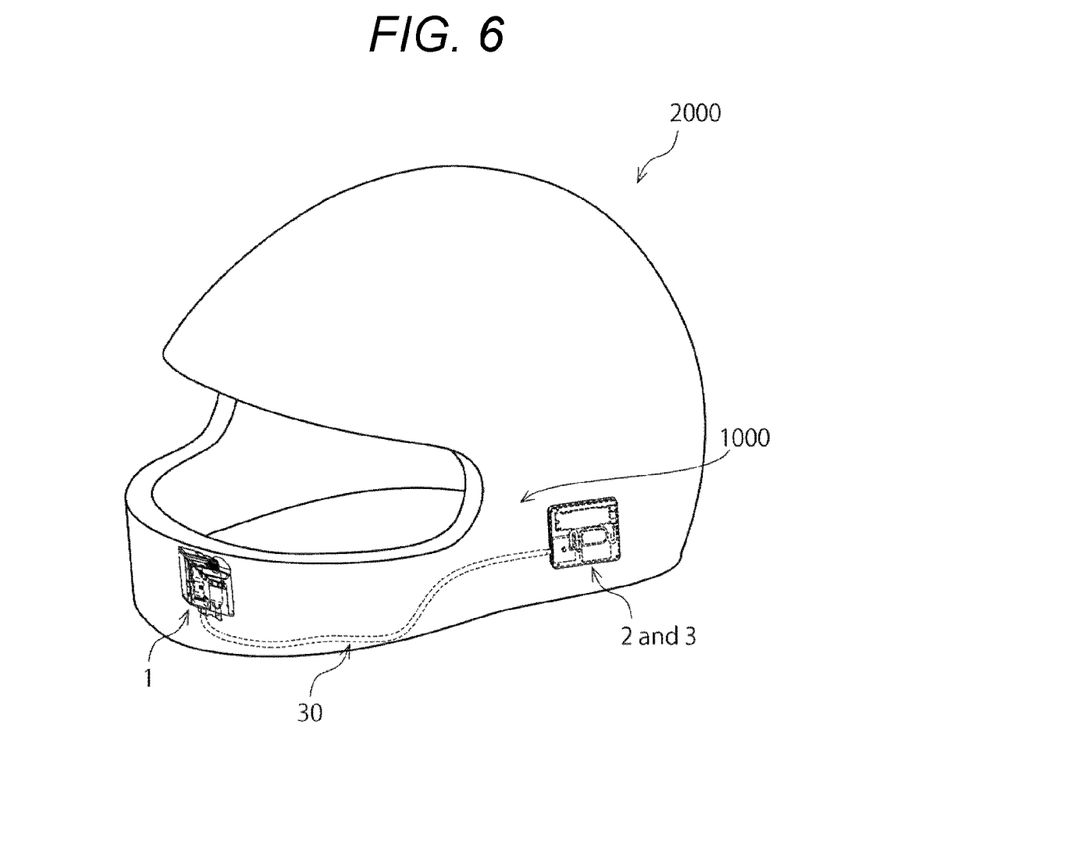
FIG. 6 is a view illustrating an exemplary embodiment in a case where an aroma generator 1000 is attached to a helmet 2000.

As illustrated in FIG. 6, in a case where the aroma generator 1000 is attached to a helmet 2000, for example, the air blower 3 including the control unit 2 may be provided on the side surface or the rear side of the exterior helmet, the air blower 3 may be connected to the cartridge holding unit 1 by the air-blowing pipe 30, and the cartridge holding unit 1 may be extended to a position close to the user's nose inside the helmet. In this case, each part of the aroma generator 1000 may be provided by being embedded in the helmet housing.

In this manner, with the aroma generator 1000 attached to the clothing or the helmet, it becomes possible to make a personal space fragrant and to take measures against surrounding odors.

The following is a specific example of control by the control unit 2 in a case where the sensing information is biological information.

When information indicating that a heart rate has increased is obtained from a heart rate sensor, an aroma with a relaxing effect is selected.

When information indicating that a pupil has contracted is obtained from a pupil sensor, an aroma with an effect of keeping a person awake is selected.

The following is a specific example of control by the control unit 2 in a case where the sensing information is external environment information.

When information indicating that it is rainy from a rain sensor, an aroma with a relaxing effect is selected.

When an odor or gas is detected by an odor sensor or a gas sensor for sensing exhaust gas and the like, an aroma with a relaxing effect is selected, and the aroma is discharged regularly.

When information indicating that noise in a car has become equal to or more than a reference value is obtained from a volume sensor, an aroma with a relaxing effect is selected.

When information indicating that brightness inside and outside the car has reached or exceeded a certain level within a predetermined time is obtained from an illuminance sensor, it is determined that a warning is required as the inside and the outside of the car has suddenly become dark or bright, and a predetermined aroma is selected.

When information indicating that a speed of the car has become faster than a reference value is obtained from a speed sensor, an aroma that enhances concentration is selected.

When information indicating that an inter-vehicular distance has become shorter than a reference value is obtained from a distance sensor, it is determined that a warning is required, and a predetermined aroma is selected.

When information indicating that the lateral G has become larger than a reference value is obtained from an acceleration sensor, an aroma with a relaxing effect is selected.

When a motion sensor detects that a car is driving backward or parking, an aroma with a relaxing effect is selected.

When information indicating that roughness of a road surface has become larger than a reference value is obtained from the motion sensor, an aroma with a relaxing effect is selected.

(3) Air Blower 3

The aroma generator 1000 may include the air blower 3 that blows a fragrance in the cartridge 11, as necessary. In this case, the control unit 2 automatically changes blowing intensity of the air blower 3 according to the sensing information.

Figure 7:
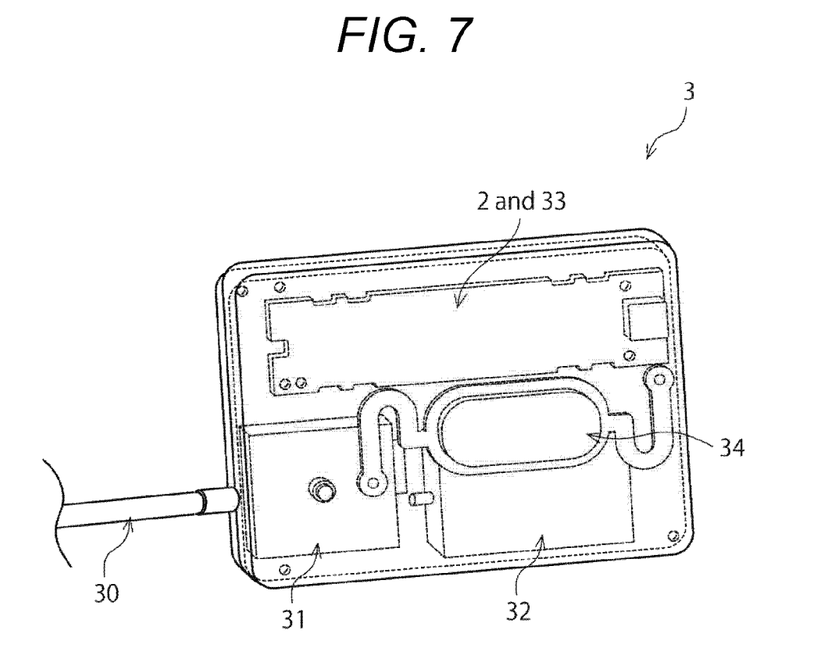
FIG. 7 is a perspective view illustrating an exemplary embodiment of an air blower 3.

FIG. 7 is a perspective view illustrating an exemplary embodiment of the air blower 3. The air blower 3 includes the air-blowing pipe 30 outside, and includes an air pump 31, a battery 32, a control board 33, and the like inside.

The air-blowing pipe 30 connects the cartridge holding unit 1 and the air blower 3, and delivers the air introduced from the air pump 31 to the cartridge 11 via the air-blowing flow path 15 described above. Furthermore, the air pump 31 is an aspect of the ventilation source, which is driven by the electric power supplied from the battery 32 to introduce air into the air-blowing flow path 15. The air pump 31 may be, for example, a diaphragm pump that deforms a diaphragm by supplying an alternating current to a piezoelectric element to suck and pump air. The battery 32 may be an electric cell that is only discharged and can be replaced, or may be a secondary battery that can be charged and discharged.

The drive of the air pump 31 may be turned on and off by a switch operation unit 34 provided in the air blower 3 being operated. In this case, for example, a switching element of the control board 33 is electrically connected by the switch operation unit 34 being pressed, and electric power is supplied from the battery 32 to the air pump 31. With this arrangement, air is supplied to the cartridge 11 via the air-blowing flow path 15.

Note that the control unit 2 and the control board 33 may be integrally configured in the case of the present embodiment.

In this case, for example, energization may be switched on and off each time the switch operation unit 34 is pressed repeatedly, or the energization may be maintained in the on state while the switch operation unit 34 is pressed. Other electronic components, such as those exemplified by a light source such as a light-emitting diode (LED), that indicate an operating status of the aroma generator 1000 may be mounted on the control board 33. Furthermore, a communication device may be mounted on the control board 33 to enable the aroma generator 1000 to be operated by a remote controller, a smartphone, or the like.

Note that the blower that supplies air toward the cartridge 11 is not limited to the air pump 31, and may be, for example, a blower that rotates a fan.

The battery 32 is electrically connected to the air pump 31 via the control board 33 and the switching element. The electric power of the battery 32 is supplied to the air pump 31 in response to the control by the control unit 2 or the operation of the switch operation unit 34. With this arrangement, when the air pump 31 is driven and air is flowed through the air-blowing pipe 30 to the ventilation flow path 110 of the cartridge 11, the fragrance held on the inner surface of the ventilation flow path 110 is vaporized so that the aroma is released together with the air, whereby the aroma can be provided to the user.

The aroma generator 1000 may include a plurality of the air blowers 3. With this arrangement, the blowing intensity can be increased as compared with the case of one air blower 3. Furthermore, the air blower 3 can be provided for each aroma, and the aroma can be switched without using power, whereby the structure of the aroma generator 1000 can be further simplified. Moreover, by the plurality of air blowers 3 provided for each aroma being operated, a plurality of aromas can be mixed and provided to the user.

Figure 8:
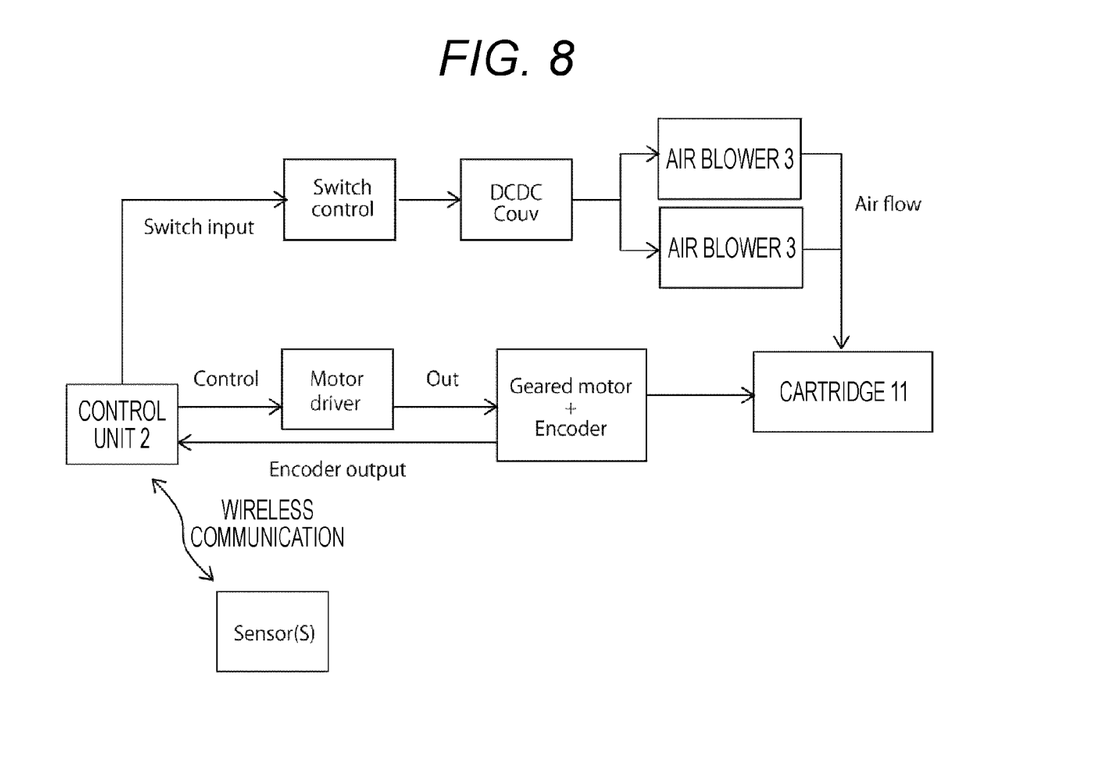
FIG. 8 is a conceptual diagram illustrating a variation of the control by the control unit 2.

Exemplary control by the control unit 2 in a case where the aroma generator 1000 includes the air blower 3 will be described with reference to FIG. 8. First, the control unit 2 transmits an on signal based on an increase in output (current value) to a switch control circuit (Switch Control) that outputs an on/off signal for controlling on/off of a switch. Then, when the switch is turned on by the on signal, the DC input current is stabilized and controlled by a DC-DC converter (DCDC Conv), and ultimately the stabilized DC power supply voltage is output to the air blower 3. In a case where there is a plurality of the air blowers 3, the DC-DC converter outputs the DC power supply voltage to each of the air blowers 3. With this arrangement, the air blower 3 is driven to generate air, and the air is introduced into the cartridge 11. Other configurations are similar to those in the case described with reference to FIG. 5, and descriptions thereof are omitted here.

Note that, in the present technology, the air blower 3 may be provided on the side of the control unit 2 as illustrated in FIG. 7, it can also be provided on the side of the cartridge holding unit 1.

(3-1) Specific Example 4

Hereinafter, the control by the control unit 2 in a case where the aroma generator 1000 includes the air blower 3 will be described more specifically.

First, the control unit 2 obtains, by wireless communication, information associated with the number of blinks, which is one of biological information, from an electrooculography sensor. This information includes, for example, that equal to or more than 40 blinks have been confirmed within one minute or the like. In response to this information, as the number has exceeded a predetermined reference value (=the number of blinks is equal to or more than 30 within one minute), the control unit 2 determines that the user is strongly feeling drowsiness and it is deeply needed to reduce the drowsiness of the user, and selects an aroma of peppermint from the fragrances held in the cartridge 11. Then, the control unit 2 rotates the cartridge 11 in the cartridge holding unit 1 using the geared motor and the encoder so that the aroma is released toward the user. At this time, since it is deeply needed to reduce the drowsiness of the user, the control unit 2 transmits an on signal based on the increase in output (current value) to the switch control circuit, thereby outputting the DC power supply voltage to the air blower 3 via the DC-DC converter to increase the air volume of the air blower 3.

Note that the control unit 2 may control blowing timing and/or a blowing time from the air blower 3 in addition to the blowing intensity from the air blower 3. In this case, a blowing start and a blowing end may be switched by a switch operation unit 214 provided in the air blower 3 or the operation unit 5 to be described later being operated. With this arrangement, it becomes possible to improve safety in a case where the user is driving and to alleviate stress on the user on the basis of the simplified operation.

(4) Display Unit 4

Figure 9:
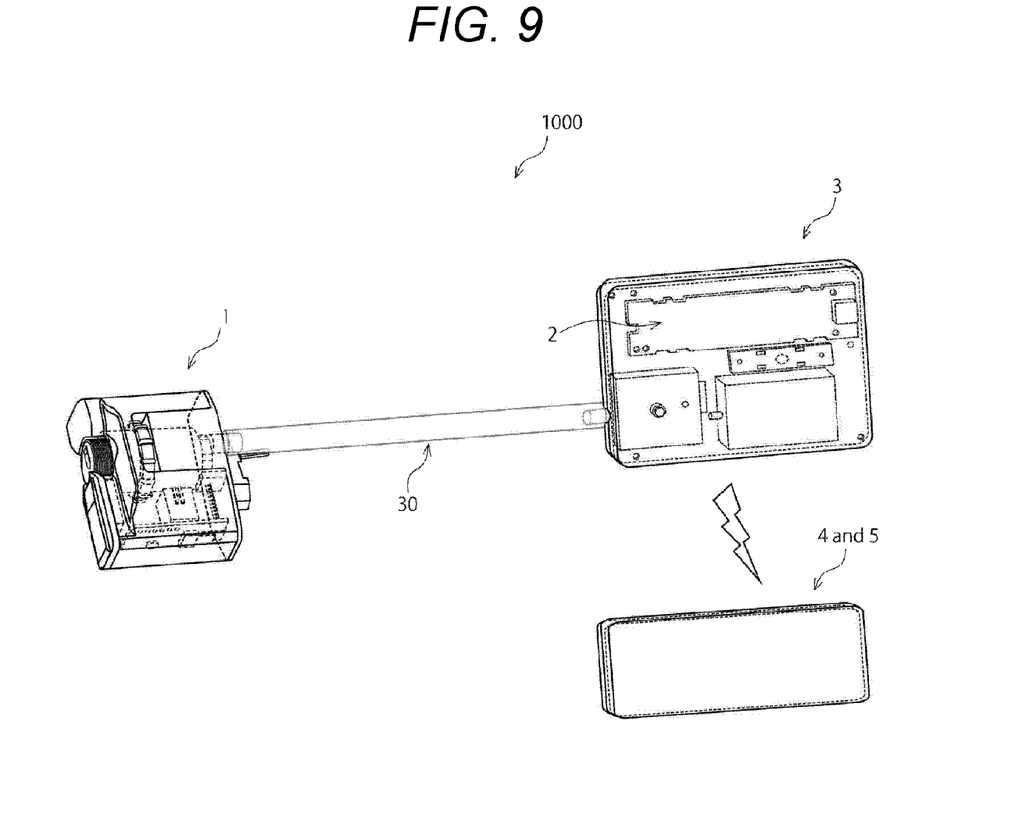
FIG. 9 is a view illustrating an exemplary embodiment of the aroma generator 1000.

FIG. 9 is a view illustrating an exemplary embodiment of the aroma generator 1000. As illustrated in FIG. 9, the aroma generator 1000 may further include the display unit 4 that displays information associated with the cartridge 11 and/or the sensing information, as necessary. With this arrangement, the user can instantly confirm those pieces of information, which improves usability.

The display unit 4 is, for example, a display device such as a liquid crystal display (LCD) and an organic electroluminescence (EL) display, which presents, under the control of the control unit 2 described above, various kinds of information to the user using images, sounds, colors, and the like.

While examples of the information associated with the cartridge 11 include a type of the cartridge 11, a type of the fragrance, a remaining amount of the fragrance, and an opening deadline of the cartridge 11, they are not limited thereto in the present technology. The sensing information is similar to that described above, and the descriptions thereof are omitted here.

While the connection between the control unit 2 and the display unit 4 can be wired communication or wireless communication in the present technology, wireless communication is preferable because disconnection is unlikely to occur and the device configuration can be simplified.

(5) Operation Unit 5

As illustrated in FIG. 9, the aroma generator 1000 may further include the operation unit 5 that selects a type of the fragrance in the cartridge 11, as necessary. With this arrangement, the user can personally select a type of the fragrance through the operation unit 5, and the aroma can be switched without exposing the cartridge holding unit 1. Furthermore, the aroma switching operation is simplified and becomes comfortable, which improves usability.

The operation unit 5 is, for example, a touch sensor based on various schemes, which detects contact given by the user on the screen of the display unit 4 described above, and provides it to the control unit 2 as an operation input.

The operation unit 5 can select a type of the fragrance in the cartridge 11 using an application installed in the operation unit 5, for example. With this arrangement, the operation efficiency can be improved.

The operation unit 5 is not an essential configuration in the present technology, and for example, an application capable of selecting a type of the fragrance in the cartridge 11 may be installed in a mobile information terminal, such as a smartphone and a tablet, to use the mobile information terminal instead of the operation unit 5.

In this case, the aroma generator 1000 and the mobile information terminal may operate in a ganged manner, and for example, when the control unit 2 detects that there has been an incoming call to the mobile information terminal, a predetermined aroma may be ejected from the cartridge 11, and the action may be used as an alert function.

Figure 10:
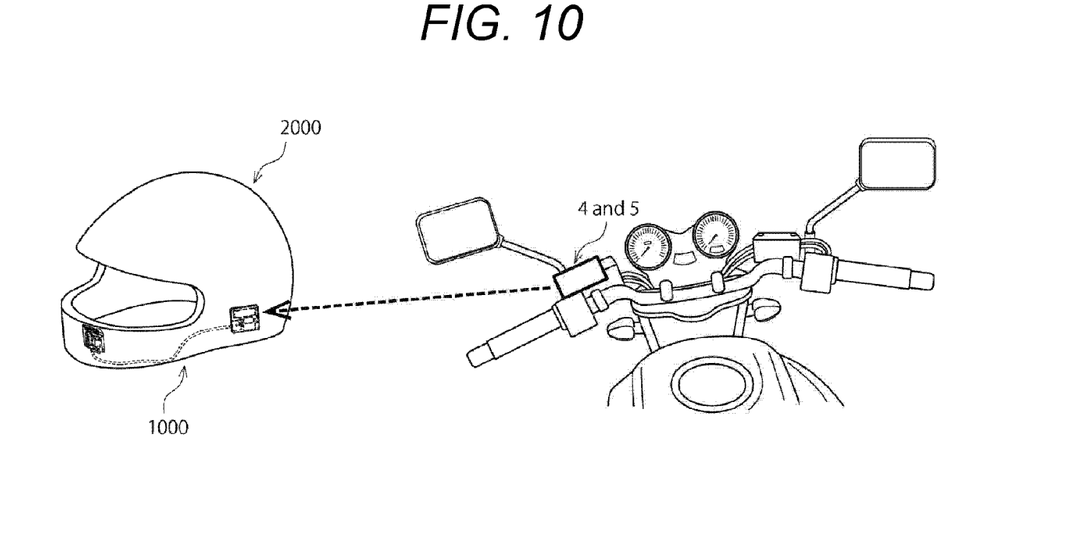
FIG. 10 is a view illustrating an exemplary embodiment in a case where an operation unit 5 is attached to a mobile object.

FIG. 10 is a view illustrating an exemplary embodiment in a case where the operation unit 5 is attached to a mobile object. In a case where the aroma generator 1000 includes the operation unit 5, the operation unit 5 may be provided on a handle of the mobile object, and a driver may operate the operation unit 5, whereby signals from the operation unit 5 may be transmitted to the control unit 2 by wireless communication. With this arrangement, the user can easily control the type of the aroma, the blowing intensity, and the like. Furthermore, as illustrated in FIG. 10, the display unit 4 and the operation unit 5 may be integrally configured in the present technology.

2. Variation of Aroma Generator 1000

Figure 11:
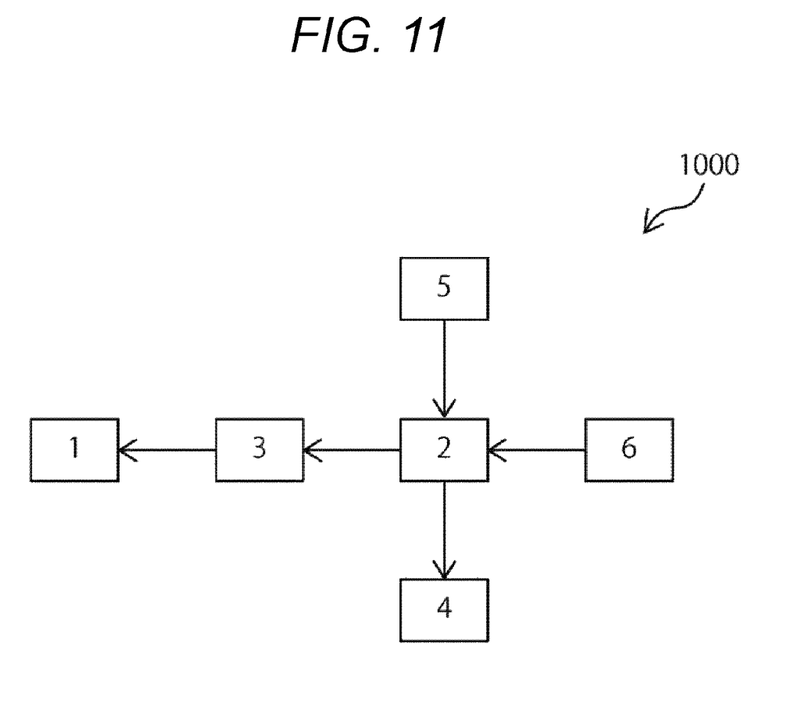
FIG. 11 is a conceptual diagram illustrating an exemplary configuration of a variation of the aroma generator 1000.

FIG. 11 is a conceptual diagram illustrating an exemplary configuration of a variation of the aroma generator 1000. In this variation, the aroma generator 1000 includes a sensing unit 6 in addition to the cartridge holding unit 1 and the control unit 2 described above. Furthermore, the air blower 3, the display unit 4, the operation unit 5, and the like may be provided, as necessary.

(1) Sensing Unit 6

The sensing unit 6 obtains sensing information. The sensing unit includes, for example, various sensors (detectors). The sensors are similar to those described above, and the descriptions thereof are omitted here. Note that, in the present technology, a plurality of the sensing units 6 may be provided.

While signal transmission from the sensing unit 6 to the control unit 2 can be wired communication or wireless communication in the present technology, wireless communication is preferable because disconnection is unlikely to occur and the device configuration can be simplified.

The cartridge holding unit 1, the control unit 2, the air blower 3, the display unit 4, and the operation unit 5 are similar to those described above, and the descriptions thereof are omitted here.

Note that the present technology can also employ the following configurations.

(1)

An aroma generator including:

a cartridge holding unit equipped with a cartridge that holds a fragrance; and a control unit that automatically selects a type of the fragrance in the cartridge according to sensing information obtained from the outside.

(2)

The aroma generator according to (1), in which the sensing information is external environment information and/or biological information.

(3)

The aroma generator according to (1) or (2), further including an air blower that blows the fragrance in the cartridge, in which the control unit automatically changes blowing intensity of the air blower according to the sensing information.

(4)

The aroma generator according to (3), in which the aroma generator includes a plurality of the air blowers.

(5)

The aroma generator according to (3) or (4), in which the control unit controls blowing timing and/or a blowing time from the air blower.

(6)

The aroma generator according to any one of (1) to (5), further including a display unit that displays information associated with the cartridge and/or the sensing information.

(7)

The aroma generator according to (6), in which the control unit wirelessly communicates with the display unit.

(8)

The aroma generator according to any one of (1) to (7), further including an operation unit that selects a type of the fragrance in the cartridge.

(9)

The aroma generator according to (8), in which the operation unit selects a type of the fragrance in the cartridge using an application.

(10)

The aroma generator according to any one of (1) to (9), which is attached to a mobile object.

(11)

The aroma generator according to (10), in which the mobile object is a car, a motorcycle, or a bicycle.

(12)

The aroma generator according to (11), in which the sensing information is any one or more pieces of information selected from a group including a speed, an acceleration level, and an angle with the ground of the car, the motorcycle, or the bicycle.

(13)

The aroma generator according to any one of (1) to (9), which is attached to clothing or a helmet.

(14)

The aroma generator according to any one of (1) to (13), in which the control unit wirelessly communicates with an external network, and causes AI on the external network to perform machine learning.

(15)

An aroma generator including:

a cartridge holding unit equipped with a cartridge that holds a fragrance;

a sensing unit that obtains sensing information; and a control unit that automatically selects a type of the fragrance in the cartridge according to the sensing information obtained by the sensing unit.

REFERENCE SIGNS LIST

1000 Aroma generator
1 Cartridge holding unit
11 Cartridge
110 Ventilation flow path
111 Main body
112 Axial hole
113 Part where formation of a ventilation flow path is omitted
114 Locking groove
12 Cartridge fixing mechanism
13 Cartridge holder
14 Cartridge holder fixing mechanism
15 Air-blowing flow path
2 Control unit
3 Air blower
30 Air-blowing pipe
31 Air pump
32 Battery
33 Control board
34 Switch operation unit
4 Display unit
5 Operation unit
6 Sensing unit
2000 Helmet

The invention claimed is:

1. An aroma generator, comprising:
a cartridge holding unit that comprises a cartridge that holds a plurality of fragrances, wherein
the cartridge comprises a plurality of ventilation flow paths that each hold a fragrance of the plurality of fragrances, and
the cartridge is rotatable within the cartridge holding unit;
an air-blowing flow path configured to communicate with one of the plurality of ventilation flow paths to blow air through the cartridge; and
circuitry configured to select one type of fragrance from the plurality of fragrances in the cartridge based on sensing information, wherein the selection comprises a rotation of the cartridge to switch a ventilation flow path of the plurality of ventilation flow paths that communicates with the air-blowing flow path.

2. The aroma generator according to claim 1, wherein the sensing information includes at least one of external environment information or biological information.

3. The aroma generator according to claim 1, further comprising an air blower configured to blow the air in the cartridge through the air-blowing flow path, wherein the circuitry is further configured to change a blowing intensity of the air blower based on the sensing information.

4. The aroma generator according to claim 3, wherein the aroma generator comprises a plurality of air blowers including the air blower.

5. The aroma generator according to claim 3, wherein the circuitry is further configured to control at least one of a blowing timing or a blowing time from the air blower.

6. The aroma generator according to claim 1, further comprising a display device configured to display information associated with at least one of the cartridge or the sensing information.

7. The aroma generator according to claim 6, wherein the circuitry is further configured to wirelessly communicate with the display device.

8. The aroma generator according to claim 1, wherein the circuitry is further configured to select the one type of the fragrance in the cartridge based on a user operation.

9. The aroma generator according to claim 8, wherein the circuitry is further configured to receive the user operation using an application.

10. The aroma generator according to claim 1, wherein the aroma generator is attachable to a mobile object.

11. The aroma generator according to claim 10, wherein the mobile object includes one of a car, a motorcycle, or a bicycle.

12. The aroma generator according to claim 11, wherein the sensing information includes one of a speed, an acceleration level, or an angle with ground of the mobile object.

13. The aroma generator according to claim 1, wherein the aroma generator is attachable to one of clothing or a helmet.

14. The aroma generator according to claim 1, wherein the circuitry is further configured to:
- wirelessly communicate with an external network; and
- control an artificial intelligence (AI) model on the external network to perform machine learning.

15. The aroma generator according to claim 1, wherein the circuitry is further configured to:
- concurrently receive a plurality of pieces of the sensing information;
- prioritize at least one piece of the sensing information among the plurality of pieces of the sensing information; and
- select the one type of the fragrance from the plurality of fragrances in the cartridge based on the prioritized at least one piece of the sensing information.

16. An aroma generator, comprising:
- a cartridge holding unit that comprises a cartridge that holds a plurality of fragrances, wherein
- the cartridge comprises a plurality of ventilation flow paths that each hold a fragrance of the plurality of fragrances, and
- the cartridge is rotatable within the cartridge holding unit;
- a sensor configured to obtain sensing information;
- an air-blowing flow path configured to communicate with one of the plurality of ventilation flow paths to blow air through the cartridge; and
- circuitry configured to select one type of fragrance from the plurality of fragrances in the cartridge based on the sensing information, wherein the selection comprises a rotation of the cartridge to switch a ventilation flow path of the plurality of ventilation flow paths that communicates with the air-blowing flow path.

\* \* \* \* \*